(12) United States Patent  
Rosemberg

(10) Patent No.: US 8,321,009 B2
(45) Date of Patent: Nov. 27, 2012

(54) DC TISSUE TREATMENT

(75) Inventor: Yossef Rosemberg, Raanana (IL)

(73) Assignee: EC-Point Medical, Inc., Henderson, NV (US)

( * ) Notice: Subject to any disclaimer, the term of this patent is extended or adjusted under 35 U.S.C. 154(b) by 958 days.

(21) Appl. No.: 11/918,712

(22) PCT Filed: Apr. 20, 2006

(86) PCT No.: PCT/IL2006/000484
§ 371 (c)(1),
(2), (4) Date: Jan. 13, 2009

(87) PCT Pub. No.: WO2006/111968
PCT Pub. Date: Oct. 26, 2006

(65) Prior Publication Data
US 2009/0125025 A1 May 14, 2009

Related U.S. Application Data

(60) Provisional application No. 60/673,781, filed on Apr. 22, 2005, provisional application No. 60/763,379, filed on Jan. 31, 2006.

(51) Int. Cl.
A61N 1/30 (2006.01)

(52) U.S. Cl. ........................................... 604/20

(58) Field of Classification Search ............... 604/20–21; 435/173.5–173.6; 607/153
See application file for complete search history.

(56) References Cited

U.S. PATENT DOCUMENTS 4,585,652 A 4/1986 Miller et al.
5,871,460 A 2/1999 Phipps et al.
5,983,131 A * 11/1999 Weaver et al. .................. 604/20

OTHER PUBLICATIONS

International Search Report for International Application No. PCT/IL2006/000484/ mailed Feb. 5, 2007; (1 page).

* cited by examiner

Primary Examiner — Manuel Mendez
(74) Attorney, Agent, or Firm — Jordan IP Law, LLC

(57) ABSTRACT

Disclosed are a method and a device useful for performing cosmetic or medical procedures of an in vivo portion of tissue. The method includes contacting an in vivo portion of tissue with a portion of a pad, substantially saturating the pad with a reactant, contacting the pad with a first electrode so that the first electrode is proximate to the portion of the pad proximate to the in vivo portion of tissue. The method further includes contacting the pad with a second electrode so as to provide an electrical path between the first electrode and the second electrode through the reactant, passing a DC voltage through a circuit including the first electrode, the reactant and the second electrode, thereby forming at least one of: an electrolytic effect, and an electrolytic product of the reactant, proximate to the first electrode.

22 Claims, 6 Drawing Sheets

DC TISSUE TREATMENT

FIELD OF THE INVENTION

The present invention relates to apparatuses and methods for delivering relatively high direct current for therapeutic treatment of tissue.

BACKGROUND OF THE INVENTION

The use of electricity in cosmetology and medicine are well-known: continuous or pulsed low voltage direct current (DC) being used for electrolytic therapy and/or deposition of substances in tissue and AC being used for cutting tissue.

Electrolytic treatments of tissue include, inter alia, use of the following procedures and definitions as used herein:

1. Electrophoresis: the movement of suspended particles through a fluid or gel under the action of an electromotive force applied to electrodes in contact with the suspension.
2. Iontophoresis: the introduction of an ionized substance (such as an active pharmaceutical ingredient) through intact skin by the application of a direct electric current.
3. Electroosmosis: the movement of a liquid out of or through a biological membrane under the influence of an electric field wherein non-charged solutes move along an electro-osmotically induced gradient.
4. Electrolytic desiccation: the removal of water from tissue using an electric current to move an electrolyte desiccant into the tissue.
5. Electokinesis: the motion of particles or liquids that results from or produces a difference of electric potential.
6. Electro-epilation: the use of electrical current to remove hair.
7. Electro-onychomycotomy: the use of electrical current to treat a fungus infection of the nail.

Electrolytic treatments are restricted to using low voltage DC because high voltage DC interferes with nerve and muscle activity, causing pain and tissue damage.

Low voltage DC, though, is an inefficient means of electrolytically affecting tissue, often resulting in deposition of insufficient amounts of a therapeutic substance in the tissue. Alternatively, to achieve sufficient deposition of the substance, low voltage DC requires a lengthy period of time that can be intolerable to a recipient while causing inefficient use of caregiver facilities.

Dispensing electrolytic treatment even using low voltage DC is not completely risk free. For example, low voltage DC electrophoresis that is inadvertently discharged near the heart may cause potentially fatal fibrillation of the ventricles. Additionally, since electrons do not travel in water, reactions at the tissue-electrode interface generally produce oxidation-reduction in substrates that are in contact with the electrodes, often resulting in tissue damage.

In spite of the drawbacks, including the inefficient and lengthy treatments, there are cosmetic treatments that currently use electrolytic DC, for example:

Hyperhydrosis

Primary hyperhydrosis, the overproduction of perspiration, occurs over various body surfaces, including palmar, axillary, plantar, facial, and truncal surfaces. Light to moderate hyperhydrosis is typically treated with applications of 25% aluminum chloride applications several times weekly. Hyperhydrosis that is recalcitrant to topical applications is often treated with iontophoresis.

Electrolytic treatments use devices that supply low DC voltage at 15-18 mA, thereby causing iontophoresis of a solution that typically include aluminum chloride. Treatments last 20-30 minutes each and are provided several times weekly. Resolution of symptoms and patient satisfaction vary considerably: many considering the treatments too time-consuming, inefficient, and/or expensive There are two types of sweat glands, eccrine and apocrine. Eccrine sweat glands open to the skin, are under sympathetic cholinergic control, and respond to both thermal and psychological stimulus. Apocrine sweat glands, associated with mammalian sexual scent, are larger than eccrine glands, open to hair follicles, and innervated by sympathetic adrenergic nerve fibers. It is highly likely that eccrine glands respond to different electrical components of iontophoresis than apocrine glands. Not only would a treatment be dispensed more rapidly with a more efficient iontophoretic unit, but also better results could accrue with dual currents: a first for apocrine sweat glands, and a second for eccrine sweat glands.

Potential for Electrolytic Treatments

In addition to iontophoresis for treatment of hyperhydrosis, there are a number of cosmetic treatments that would potentially benefit from a more efficient and efficacious DC electrolytic apparatus.

Electro-Epilation

Referring to FIG. 1, a hair 204 grows from a follicle 208. As follicle 208 is an area where the hair shaft has not fully keratinized, follicle 208 rapidly absorbs electrolytic products.

The life cycle of follicle 208 is divided into 3 phases: anagen, catagen, and telogen. The anagen phase is the phase of active growth. The catagen phase marks regression of follicle 208, and the telogen phase represents a resting period. In the human scalp, the anagen phase lasts approximately 3-4 years. The catagen phase lasts approximately 2-3 weeks, and the telogen phase lasts approximately 3 months.

Onychomycosis

Onychomycosis is an infection that causes fingernails or toenails to thicken, discolor, disfigure, and/or split. Initially disfigurement is primarily a cosmetic concern, though without treatment, the nail can thicken, causing pressure, irritation, and pain in closed shoes.

In diabetics, onychomycosis is both common and dangerous; recent studies have shown a higher rate of amputation in diabetics with onychomycosis compared to those without the infection.

Onychomycosis is difficult to treat because nails grow slowly and receive very little blood supply. Onychomycosis pathogens generally comprise fungal and/or yeast: fungal pathogens including trichophyton rubrum and trichophyton mentagrophytes; and yeast pathogens including candida albicans and candida parapsilosis.

Topical antifungal medication requires 6 months to a year of daily treatments for the nail to regain a healthy, clear, thin appearance. Additionally, there is a relatively high rate of failure and recurrence following treatment.

A well-focused and deep electrolytic intracellular deposition of onychomycotic treatment agents would likely result in fewer treatments and less chance of recurrence.

Actinic Keratosis

Actinic keratosis is a scaly or crusty bump that forms on the skin surface on sun-exposed areas: face, ears, bald scalp, neck, backs of hands and forearms, and lips.

Actinic keratosis can be the first step in the development of skin cancer. It is estimated that up to 10 percent of active lesions, which are redder and tenderer than the rest, will take the next step and progress to squamous cell carcinoma.

The most aggressive form of keratosis, actinic cheilitis, appears on the lips and can evolve into squamous cell carcinoma. Roughly one-fifth of these chelitic-based carcinomas metastasize. More problematic, cancer in the presence of keratosis is not limited to squamous cell carcinoma, but may develop into a highly aggressive and metastatic melanoma.

Treatment is essential in order to avoid the potentially more invasive and extensive treatment of a subsequent malignancy. Current treatments of actinic keratosis include curettage, shave removal, cryosurgery chemical peels and topical creams, for example creams including 5-fluorouracil (5-FU). Each type of treatment is associated with varying initial success but a high rate of return several months to several years down the road.

Actinic keratosis treatment must reach the root of the keratosis in the skin basement membrane to be effective. One theory on why actinic keratosis returns following removal is that the above-noted treatments are not carried down to a sufficient depth due to fear of causing skin scarring. An electrolytic system that deposits medication in and below the basement membrane has greater potential to successfully treat actinic keratosis; without recurrence and without the trauma of ablation or cutting.

Inoperable Tumors

An example of a tumor that is rarely, if ever, surgically excised is a cancerous liver tumor. Surgical excision of liver cancer is not an option because during the surgery, leukemia cells associated with the cancer easily spread to all the organs via the blood stream and the lymph vessels.

There are two main kinds of liver cancer, hepatoma and cholangiocarcinoma. Hepatoma is cancer of the hepatocytes, the main functioning liver cell. Hepatoma is primary liver cancer. Hepatoma usually grows in the liver as a ball-like tumor, invading the normal tissue surrounding it. A history of infection with the hepatitis B virus puts individuals at risk of developing hepatoma.

Cholangiocarcinoma is cancer of the bile duct cells. Cholangiocarcinoma originates in the bile ducts and is often caused by infestation with liver fluke, a parasite called Clonorchis. The cancer grows along the bile ducts in sheets or lines, and is hard to find on X-ray studies.

Most cases of liver cancer are metastases from another organ. Because of its very high blood flow and many biological functions, the liver is one of the most common places for metastases to grow. Tumors that originally arise in the colon, pancreas, stomach, lung, or breast often spread to the liver.

Treatment of liver cancer varies according to the tumor size. Tumors less than 5 cm in diameter are often destroyed using ethanol or acetic acid injected into the tumor.

For tumors greater than 5 cm, a first line treatment for hepatic carcinoma is often chemotherapy where cytotoxic active pharmaceutical ingredients (APIs) are used to destroy cancer cells. APIs are usually given intravenously directly into the hepatic artery during each dhemotherapy session. A session typically lasts a few days, followed by recovery period from the side effects. The number of sessions depends on the type of liver cancer and how well it is responding to the APIs.

Chemotherapy APIs often concentrate in fast growing non-liver tissues, causing unpleasant side effects including reduced resistance to infection, nausea, sore mouth and hair loss.

Radiation therapy, often used in conjunction with chemotherapy or lesions above 5 cm, uses X-rays or other high-energy rays to kill cancer cells and shrink tumors. Radiation therapy often adds to chemotherapy side effects.

An electrolytic system that deposits cytotoxic medication with liver tissue has great potential to treat liver cancer, increasing survival rates and reducing side effects.

Electrolytic Alternatives to DC

Recognizing the risk and inefficiency of DC electrolytic treatments to tissue, devices using alternating current (AC) are often used for electrolytic treatment. However, because low frequency AC is accompanied by pain and causes muscle and nerve damage, AC can only be dispensed at higher frequencies.

Medically useful, and safe, high frequency AC has been determined as a current having a frequency of 10,000 or more cycles per second, thereby causing no muscular contractions and having no affect on nerves. In recognition of the damage caused by low frequency AC, regulatory agencies generally limit AC therapeutic modalities to high frequency AC above 10 MHz.

High frequency AC, though, is not useful for electrophoresis procedures because during oscillation, AC constantly changes polarity, causing cell membranes to block electrophoretic movement. The drawbacks of high frequency AC, therefore, limit its use to tissue treatments that require high temperatures. AC, for example, is used to generate heat for cutting tissue, cauterizing bleeding vessels and/or destroying unwanted tissue, including electro-epilation.

U.S. Patent Application published as U.S. 2001023330 teaches a transdermal AC iontophoresis assembly that dispenses pulsed AC frequencies below 100 Hz. However, to limit tissue damage, each pulse duration is less than 2 milliseconds, thereby reducing deposition and increasing treatment time similar to low voltage DC treatments.

U.S. Pat. No. 6,553,253 teaches electrokinetic delivery of therapeutic substances into tissue using AC rectified into DC at a frequency below 1 megahertz. Since this low frequency poses a danger of causing ventricle fibrillation, professional administration is required.

PCT patent application published as WO 2003/103522 teaches injecting a substance into a tissue and providing electrolytic treatments by using the injector as a first electrode in combination with a second remote electrode, similar to mono-polar electrosurgical system.

Articles, included by reference in their entirety, providing background for the present invention, include:

Rosemberg, Y. and Korenstein, R. "Incorporation of macromolecules into cells and vesicles by low electric fields: induction of endocytotic-like process" in Bioelchem. Biophys. Res. Comm. 1997, 42, 275-281

Antov Y, Barbul A, Mantsur H, and Korenstein R. "Electroendocytosis: exposure of cells to pulsed low electric fields enhances adsorption and uptake of macromolecules" in Biophysical Journal 2005, 88(3), 2206-2223.

Entin I, Plotnikov A, Korenstein R, Keisari Y. "Tumor growth retardation, cure, and induction of antitumor immunity in B16 melanoma-bearing mice by low electric field-enhanced chemotherapy" in *Clinical Cancer Research* 2003, 9(8), 3190-3197.

Nordenstrom B E. "Electrochemical treatment of cancer: Variable response to anodic and cathodic fields" American Journal of Clinical Oncology. 1989 December; 12 (6):530-6; as well as U.S. Pat. Nos. 4,289,135, 4,572,214 and 4,974,595 and China Patent 1042838 to Nordenstrom, et al.

Patents that provide background to the present invention include:

U.S. Pat. No. 6,063,076, "Method and system for removal of hair" using electromagnetic energy to destroy hair matrix;

U.S. Pat. No. 4,155,363 "Electronically controlled apparatus for electrolytic depilation" using electric current that is interrupted between 1 to 3 seconds;

U.S. Pat. No. 5,443,441 "Apparatus and method for transdermal delivery of cosmetic compositions" uses electric current in a range of about 0.1 mA to about 10 mA;

U.S. Pat. No. 6,039,746 "Patch electrolysis system and method for removing hair from skin" applies an electrolysis current through patches secured to a skin surface;

European Patent EP 0824003 "Hair removal device and method" relies on iontophoretic deposition of thioglycolate depilatories;

PCT publication WO 2001/87171 "Method and System for Removal of Hair with a Conductive Layer" uses electromagnetic energy to destroy hair matrix;

European Patent EP 0783347 "Method of Hair Removal" by removing the hair and treating the exposed follicle to inhibit hair regeneration; and In spite of the tremendous need and advantage for efficient and fast electrolytic treatment of tissue, there is no apparatus that provides electrolytic tissue treatment devoid of the above limitations.

SUMMARY OF THE INVENTION

Embodiments of the present invention successfully address at least some of the shortcomings of the prior art by providing methods and apparatuses for efficient and fast electrolytic treatment of tissue using high current that is dispensed without the above-noted problems.

According to an aspect of the invention, electrolytic tissue apparatus and treatment methods are provided; wherein the apparatus comprises an Electrolytic Conversion Device (ECD) including a reactant, at least a portion of the reactant being electrolysable. The ECD further includes a pad substantially soaked with the reactant, the pad having a lower pad surface, a first electrically insulating layer having an upper insulation surface substantially in contact with the lower pad surface and a first opening passing through the insulating layer. In addition, the ECD includes two terminals comprising first and second terminals configured for connecting to a DC power source, at least two electrodes substantially contacting the pad and spaced a distance from each other, such that a first electrode connected to the first terminal contacts the pad substantially proximate to the first opening, and a second electrode connected to the second terminal contacts the pad substantially distant from the first opening.

In exemplary embodiments, the apparatus further comprises a DC power source connected to the two terminals so that the first electrode is an anode. Optionally, the DC power source is connected to the terminals so that the first electrode is a cathode.

In a further exemplary embodiment, the pad proximate to the first opening is compliant; comprising a material selected from the group consisting of woven cloth, non-woven cloth, fabric, fibers, spongy material, rubber, cotton, wool, polyester and polyamide.

Optionally, the first opening has a shape selected from the group consisting of square, oval, circular, round, rectangular, curved, triangular, circular section and arced.

In an additional exemplary embodiment, at least a portion of the reactant is a solution and reactant includes at least one of an API and a salt. Optionally, the reactant comprises at least one of the group consisting of an anti-mitotic agent, a photo-reactive agent, an enzyme, an atomic particle-emitting substance, an antigenically tagged API a cell receptor tagged API and a genetically tagged API. In an alterative exemplary embodiment, the reactant comprises at least one of the group consisting of a desiccator, an epilator, an anti-fungal agent, and a catalyst.

In some exemplary embodiments, a product of electrolysis of the reactant comprises at least one of the group consisting of an anti-mitotic agent, a photoreactive agent, an enzyme, an atomic particle-emitting substance, an antigenically tagged API, a cell receptor tagged API and a genetically tagged API. Alternatively, a product of electrolysis of the reactant comprises at least one of the group consisting of desiccator, epilator, anti-fungal agent, and a catalyst. In some embodiments, at least a portion of the reactant is susceptible to at least one of the group consisting of electrophoresis, iontophoresis, electroosmosis, and electokinesis.

In exemplary embodiments, at least a portion of the first electrically insulating layer is of a material comprising a material having a property selected from the group consisting of compliant, flexible, plastic, and rigid. Optionally, at least a portion of the first electrically insulating layer is impermeable to the passage of gas.

In alternative exemplary embodiments, at least a portion of the first electrically insulating layer is of a material comprising a material from the group consisting of foil, film, sheet, membrane, non-woven cloth, and woven cloth. Optionally, the first insulating material is selected from the group consisting of paper, polyester, polyethylene, polypropylene and silicone. Additionally the first insulating layer has a thickness of less than about 5 μm. Alternatively, the first insulating layer has a thickness of less than about 100 μm. In still other embodiments, the first insulating layer has a thickness of more than about 5 μm. In yet other embodiments, the first insulating layer has a thickness of more than about 100 μm.

Optionally, the insulating material is cuttable.

In further exemplary embodiments, the first insulating layer includes a lower surface substantially in contact with a first base layer, the first base layer having a first opening substantially aligned with the insulation layer first opening.

Optionally, the first base layer has a thickness of less than about 15 μm. Alternatively, the first base layer has a thickness of less than about 100 μm. In still alternative embodiments, the first base layer has a thickness of no more than about 15 μm; or additionally, the first base layer has a thickness of no more than about 100 μm.

In exemplary embodiments, at least a portion of the first base layer is selected from the group consisting of aluminum, stainless steel, noble metal, and plastic.

In some exemplary embodiments, a second electrically insulating layer is included wherein the at least two electrodes and the pad are contained between the first electrically insulating layer and second electrically insulating layer.

Optionally, the second electrically insulating layer is substantially contiguous with the first electrically insulating layer, thereby together substantially containing the pad and the at least two electrodes.

In some embodiments, a second base layer substantially covers the second insulating layer. Further, at least a portion of the second base layer is selected from the group consisting of aluminum, stainless steel, noble metal, and plastic. Optionally the second base layer is substantially contiguous with the first base layer, thereby substantially electrically sealing at least a portion the first and second insulating layers.

In an exemplary embodiment, the apparatus further comprises a DC power source connected to the terminals; the DC power source provides at least about 1 volt. Alternatively, the DC power source provides at least about 2 volts; even at least about 4 volts; or even at least about 6 volts.

In alternative embodiments, the DC power source provides no more than about 40 volts; or the DC power source provides no more than about 60 volts. Optionally the DC power source provides no more than about 80 volts; or the DC power source provides no more than about 100 volts.

In some additional exemplary embodiments, the DC source is configured to provide a current of at least about 0.1 mA; or the DC source is configured to provide a current of at least about 2 mA. Alternatively the DC source is configured to provide a current of at least about 3 mA; or the DC source is configured to provide a current of at least about 4 mA. Further, the DC source is configured to provide a current of no more than about 100 mA; or the DC source is configured to provide a current of no more than about 250 mA. In still other embodiments the DC source is configured to provide a current of no more than about 500 mA; or the DC source is configured to provide a current of no more than about 1000 mA.

In an exemplary embodiment, the DC source is configured to provide a continuous current. Alternatively, the DC source is configured to provide a pulsed current and the current has a pulse width of at least about $1\times10^{-5}$ seconds. In other embodiments the current has a pulse width of at least about $3\times10^{-9}$ seconds. In still other embodiments, the current has a pulse width of no more than about 0.1 second. In still other embodiments, the current has a pulse width of no more than about 0.01 second. And in other embodiments, the current has a pulse width of no more than about $1\times10^{-5}$ seconds. Further, in other embodiments, the current has a pulse width of no more than about $3\times10^{-9}$ seconds.

In some exemplary embodiments the upper insulation layer, the pad, and the lower insulation layer constitute a substantially planar laminated construct. Optionally, the substantially planar laminated construct is substantially flexible.

In additional exemplary embodiments the first insulating layer comprises at least two angulated walls defining an internal volume there between, wherein the first electrode, the second electrode and the pad are contained within the volume. Optionally, the at least two angulated walls substantially form a needle-like configuration. Optionally, the needle-like configuration is configured to pierce tissue. Further, optionally, the apparatus is substantially implantable in vivo.

In some embodiments, the apparatus is substantially implantable in a tissue selected from the group consisting of soft tissue, bone, cartilage and liquid.

In other exemplary embodiments, the DC is provided by at least one of an AC to DC converter and a battery.

Optionally, the DC source is configured to provide a potential of at least about 1 volt. Alternatively, the DC source is configured to provide a potential of at least about 2 volts; or the DC source is configured to provide a potential of no more than about 100 volts. In still other embodiments, the DC source is configured to provide a potential of no more than about 1000 volts.

Further, in some embodiments, the DC source is configured to provide a continuous current.

In further exemplary embodiments, the apparatus includes an oscillator connected to the provided DC, the oscillator producing a pulse width of at least about $1\times10^{-5}$ seconds. In other embodiments the current has a pulse width of at least about $3\times10^{-9}$ seconds. In still other embodiments, the current has a pulse width of no more than about 0.1 second.

In still other embodiments, the current has a pulse width of no more than about 0.01 second. And in other embodiments, the current has a pulse width of no more than about $1\times10^{-5}$ seconds. Further, in other embodiments, the current has a pulse width of no more than about $3\times10^{-9}$ seconds.

In some exemplary embodiments, the apparatus includes at least one signal amplifier adapted to receive and amplify the at least one monopolar pulse. Further, the at least one signal amplifier is adapted to provide a first polarity to the first terminal, and a second polarity to the second terminal.

Optionally, the at least one signal amplifier comprises at least one of a resistor, a capacitor, and a transistor.

In some embodiments, the DC source is configured to provide a current of at least about 0.1 mA; or the DC source is configured to provide a current of at least about 2 mA. Alternatively, the DC source is configured to provide a current of at least about 3 mA or the DC source is configured to provide a current of at least about 4 mA.

In alternative exemplary embodiments the DC source is configured to provide a current of no more than about 100 mA; or the DC source is configured to provide a current of no more than about 250 mA. Alternatively, the DC source is configured to provide a current of no more than about 500 mA; or the DC source is configured to provide a current of no more than about 1000 mA.

In some exemplary embodiments, at least a portion of the first base layer is electrically conductive. Further, in alternative embodiments, the apparatus includes a side electrode in electrical contact with the electrically conductive portion of the first base layer. Optionally the side electrode is configured to produce an alternating electrical field. In some embodiments, the side electrode includes at least one inverter.

In other exemplary embodiments, the apparatus comprises at least four electrodes, including a third electrode and a fourth electrode in contact with the pad so that the third electrode is electrically connected to the fourth electrode through the reactant.

Optionally, the apparatus further comprises at least two openings, a first opening and a second opening, wherein the second opening is proximate to the third electrode.

According to an aspect of the invention, a method is provided for treating of an in vivo portion of the tissue. The method comprises contacting an in vivo tissue portion with a portion of a pad, substantially saturating the pad with a reactant. The method additionally comprising, contacting the pad with a first electrode so that the first electrode is proximate to the portion of the pad proximate to the area of tissue; contacting the pad with a second electrode so as to provide an electrical path between the first electrode and the second electrode through the reactant. The method furthermore comprising, passing a DC through a circuit including the first electrode, the reactant and the second electrode, thereby forming at least one of an electrolytic effect, and an electrolytic product of the reactant, proximate to the first electrode.

In some exemplary embodiments, the second electrode is electrically distanced from the area of tissue so as to substantially prevent passage of current through the tissue.

In other exemplary embodiments, the electrical distancing includes interposing an electrical insulator between the pad and the in vivo tissue portion in proximity of the second electrode.

In some embodiments, a voltage of the passing current provides at least about 1 volt. Alternatively, a voltage of the passing current provides at least about 2 volts; even at least about 4 volts; or even at least about 6 volts.

In alternative embodiments, a voltage of the passing current provides no more than about 40 volts; or the voltage of the passing current provides no more than about 60 volts. Optionally the voltage of the passing current provides no more than about 80 volts; or the DC power source provides no more than about 100 volts.

In some additional exemplary embodiments, a DC source is configured to provide a current of at least about 0.1 mA; or the DC source is configured to provide a current of at least about 2 mA. Alternatively the DC source is configured to provide a current of at least about 3 mA; or the DC source is configured to provide a current of at least about 4 mA. Further, the DC source is configured to provide a current of no more than about 100 mA; or the DC source is configured to provide a current of no more than about 250 mA. In still other embodiments the DC source is configured to provide a current of no more than about 500 mA; or the DC source is configured to provide a current of no more than about 1000 mA.

In some embodiments, a DC source is included that is configured to provide a continuous current.

In alternative embodiments, a DC source is configured to provide a pulsed current; and the current has a pulse width of at least about $1 \times 10^{-5}$ seconds. In other embodiments the current has a pulse width of at least about $3 \times 10^{-9}$ seconds. In still other embodiments, the current has a pulse width of no more than about 0.1 second. In still other embodiments, the current has a pulse width of no more than about 0.01 second. In other embodiments, the current has a pulse width of no more than about $1 \times 10^{-5}$ seconds. Further, in other embodiments, the current has a pulse width of no more than about $3 \times 10^{-9}$ seconds Optionally, while passing the DC, the electrolytic product migrates to form a chemoelectric gradient proximate to the first electrode along a surface of the tissue, and a first distance below the surface of the tissue.

In an exemplary embodiment, the distance the electrolytic product migrates below the surface increases with time.

In an exemplary embodiment, the method device includes a first opening having a cross sectional area and as the migration increases, the product forms a cross sectional area below the surface that is related to the first opening cross sectional area.

In some exemplary embodiments, the reactant comprises an API. Optionally, the API is selected from the group of APIs consisting of antimycotic, anti-cancer, epilation, pre-cancerous treatment and hyperhydrotic treatment APIs. In some embodiments, the antimycotic API is selected from the group consisting of miconazole, clotrimazole, econazole, ketoconazole, ciclopirox, naftifine, and terbinafine.

In other embodiments, the anti-cancer API is selected from the group consisting of anti-mitotic, photoreactive, atomic particle-emitting, antigenically tagged, and genetically altering APIs.

In an alternative embodiment, the epilation API is selected from the group consisting of Thioglycolate depilatories, Eflornithine and Hydroxyl ion producing reactants.

Optionally, the anti pre-cancerous API is selected from the group consisting of Jessners solution, trichloroacetic acid, bleomycin, hydroxyurea and 5-fluorouracil (5-FU).

In still some other embodiments, the reactant comprises a reactant selected from the group consisting of hyperhydrotic treating substances, including aluminum chloride API. In other embodiments the cancer is electrolytically treated with an anti-cancer API.

In some embodiments, the tissue includes excess hair and the reactant includes at least one epilation API.

Optionally, the tissue contains one mycotic nail fold and the reactant includes at least one antimycotic API. Alternatively, the tissue contains at least one cancer cell and the reactant includes at least one anti-cancer API.

In some further embodiments, the tissue contains at least one hyperhydrotic gland and the reactant includes at least one hyperhydrotic treating substance.

In some optional embodiments, the tissue contains at least one cell exhibiting actinic keratosis and the reactant includes at least one precancerous treating substance.

In some further embodiments, the method includes applying an AC potential to the tissue, thereby enhancing the electrolytic effect.

In some additional embodiments, the method includes providing a side electrode in contact with the tissue, applying an alternating current to the side electrode, thus increasing a rate at which the product migrates.

In some further additional embodiments, the method further includes contacting the pad with a third electrode and a fourth electrode, interposing an insulating layer between the tissue and the pad proximate to the third electrode, passing current through the third and fourth electrodes with a DC of at least about 1 mA, and migrating the first electrolytic product into a surface of the tissue proximate to the fourth electrode.

Optionally, the first and third electrodes have a first polarity and the second and fourth electrodes have an opposite polarity.

In some embodiments, a second electrolytic reactant is included wherein the first reactant reacts to a first polarity and the second reactant reacts to an opposite polarity.

According to an aspect of the invention, a method is provided for cosmetically improving an area of unaesthetic skin using an electrolytic treatment, comprising; contacting an area of unaesthetic skin with a pad, contacting the pad with a first electrode and a second electrode, interposing an insulating layer between the skin and the second electrode, and passing a DC of at least about 1 mA between the first and second electrodes, thereby cosmetically improving the area.

In some embodiments, skin is selected from the group consisting of at least one of hirsute skin, onychomycotic skin, hyperhydrotic skin, and actinic keratosis-affected skin.

Optionally, the method further includes providing a side electrode in contact with the skin, applying an alternating current to the side electrode thereby. In a further exemplary embodiment, the method further includes contacting the skin with a third electrode and a fourth electrode, passing current through the third and fourth electrodes with a DC and increasing at least one of; a rate at which the skin cosmetically improves, and an area in which the skin cosmetically improves.

Thus, embodiments of the present invention successfully address at least some of the shortcomings of presently known configurations by providing a safe and efficient apparatus and method for administering electrolytic tissue treatment; the apparatus including an electrolytic dispensing structure that prevents DC from traveling through tissue as will be explained below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention of DC Tissue Treatment is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENTS

Figure 1:
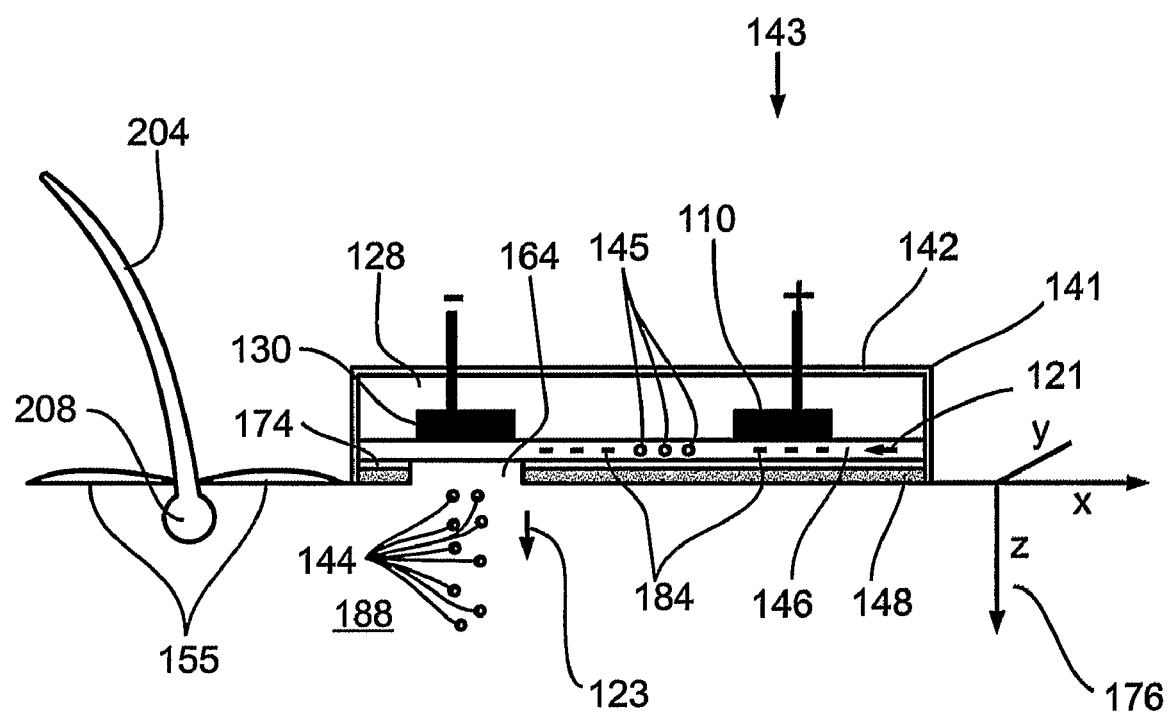
FIG. 1 is a schematic representation of an Electrolytic Conversion Device (ECD) having two electrodes, in accordance with an embodiment of the present invention.

In broad terms, the present invention relates to cosmetic and/or medical treatment of tissue using constant or pulsed DC electric current. The principles and operation of the DC tissue treatment system, according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The principles, uses and implementations of the teachings of the present invention may be better understood with reference to the accompanying description, figures and examples, perusal of which allows one skilled in the art to implement the teachings of the present invention without undue effort or experimentation. In the figures, like reference numerals refer to like parts throughout.

Generally, the nomenclature used herein and the laboratory procedures utilized in the present invention include techniques from the fields of biology, engineering, material science, medicine and physics. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the relevant arts. Implementation of the methods of the present invention involves performing or completing selected tasks or steps manually, automatically, or a combination thereof.

Figure 7:
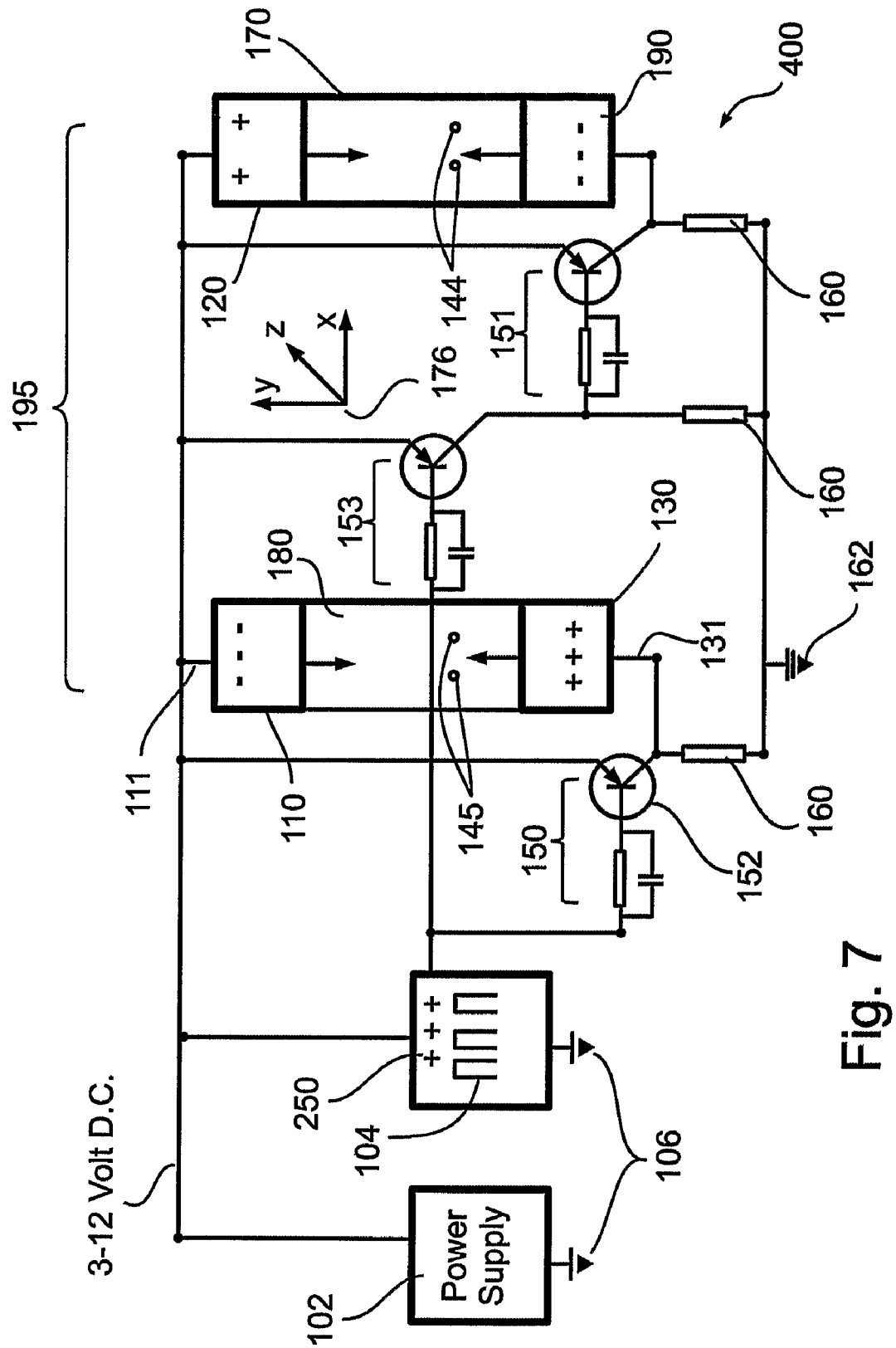
FIG. 7 is a schematic representation of an electrolytic circuit in conjunction with the ECD of FIG. 6, in accordance with an embodiment of the present invention.

The teachings of the present invention contemplate at least three embodiments of system configurations:

a system 200 including a two-electrode ECD unit (FIG. 2);
a system 300 including a three electrode ECD unit (FIG. 5); and
a system 400 including a four-electrode ECD unit (FIG. 7).

To maintain clarity, an in-depth presentation of System 200 will be followed by structural and/or procedural differences inherent in systems 300 and 400. As used herein, any structure, reactant, product electrical circuitry, or current type, voltage, amperage, and/or pulse width described with reference to system 200, is applicable mutatis mutandi to system 300 and 400.

Two Electrode Devices

Referring to FIG. 1, as used herein, an Electrolytic Conversion Device (ECD) refers to a three dimensional structure having at least one cathode 110, herein (+) electrode 110 and at least one anode 130, herein (−) electrode 130, to which pulsed or continuous DC is applied.

A 2-ECD 143 includes (+) electrode 110 in electrical contact with (−) electrode 130 through a fabric pad 146 saturated with a reactant 145; reactant 145 typically comprising an electrolytic solution containing a salt and/or an API.

Applying DC to electrodes 110 and 130 causes formation of ions 184 along pad 146 while an upper insulation prevents the DC from affecting other objects, for example, an operator's hand.

In an exemplary embodiment, pad 146 proximate to an opening 164 is compliant. Further, pad 146 may include or may essentially consist of one of more of a wide variety of materials, including woven cloth, non-woven cloth, fabric, fibers, spongy material, rubber, cotton, wool, polyester and polyamide.

In an exemplary embodiment, a base layer 148 comprises a thin material that, for example, is impermeable to liquid and gaseous reactants that form within electrolytic products 144. Base layer 148 comprises, for example aluminum, stainless steels, noble metal or plastic; noble metal as used herein referring to a metal from the group of stainless, non-stainless steel metals, including titanium, platinum, gold and nitinol.

Base layer 148 typically has a thickness of greater than about 15 µm and less than about 100 µm. Alternatively, base layer 148 has a thickness of greater than about 10 µm and no more than about 15 µm; the thicknesses being determined based upon current, voltage, and the location and type of tissue 188.

Base layer 148 is typically insulated from fabric pad 146 by an insulating layer 174 that comprises foil, paper, film, sheet, membrane, non-woven cloth, and/or woven cloth. Alternatively, insulating layer 174 comprises aluminum, stainless steel, noble metal, and plastic.

Alternatively, insulating layer 174 comprises materials that are gas impermeable, for example paper, polyester, polyethylene, polypropylene and silicone. In an alternative exemplary embodiment, mesh 174 comprises a material that is impermeable to gas for example produced along with reactant 144.

Mesh 174 typically has a thickness of greater than about 1 µm and less than about 5 µm. Alternatively, insulating layer 174 has a thickness of greater that 5 µm and less than 100 µm. In still other embodiments, insulating layer 174 has a thickness of greater that 100 µm.

Alternatively, mesh 174 has a thickness of no more than about 10 µm or no more than about 15 µm; the various thicknesses being determined based upon current, voltage, and tissue 188 location.

The combined thinness of base 148 and insulating 174 layers ensures that ions 184 and reactant 144 at opening 164 easily pass into tissue 188. Window 164 may include a wide variety of shapes, for example square, oval, circular, round, rectangular, curved, triangular, circular section and arced; for example depending on the shape of tissue 188 area to be treated. In an exemplary embodiment, in treating an onychomycotic nail, opening 164 could include an arced area to cover the nail curvature.

Optionally, an operator can cut opening 164 to a given shape. In an exemplary embodiment, the operator cuts through thin base layer 148 and thin insulation layer 146 to modify the shape of opening 164.

As is seen in FIG. 1, opening 164 has a portion of base layer 148 and insulation layer 146 on either side. In an alternative exemplary embodiment, opening 164 extends toward hair 204, such that opening 164 is completely unenclosed at the side nearest hair 204. In this embodiment, pad 146 may even protrude past a boundary 141 toward hair 204. Such an embodiment optionally being used on irritated tissue 188 wherein compliant pad 164 is tolerated by the recipient, but not harder base layer 148 and pad layer 146.

In an exemplary embodiment, at least a portion of pad 146 comprises a woven relatively flexible material, an amorphous relatively flexible material, or a porous, or a relatively rigid material.

Prior to application of 2-ECD 143, a liquid 155 is applied to the surface of tissue 188 to facilitate contact between tissue 188 and ions 184 at opening 164. Base layer 148 covers (+) electrode 110 and insulating layer 174, substantially preventing the (+) current from passing into tissue 188. Electrical connection between (+) electrode 110 and (−) electrode 130 is therefore substantially restricted to pad 148.

By substantially blocking the passage of current, 2-ECD 143 provides safety against associated dangerous cardiac events. The arrangement, whereby neither electrode 110 nor electrode 130 directly contact tissue 188, also stops any danger of polarization damage to tissue 188 noted above.

Even though relative safety is provided because electrodes 110 and 130 do not contact tissue, 2-ECD 143 incorporates additional features geared for patient comfort. For example heat from reactant 145 and/or products 144 is avoided in many treatments by running 2-ECD 143 at 10 mA to 300 mA.

Higher currents, for example above 1000 mA, might produce heat that could cause heating or boiling of reactant 145 and/or products 144, resulting in recipient discomfort and/or damage to tissue 188.

The rapid migration of products 144 into tissue 188 begins with electrolysis of reactant 145 as current passes through pad 146 between electrodes 110 and 130.

The electric field within pad 146 favors ions 184 to diffuse through pad 146 in a direction 121 and concentrate at opening 164. The concentration of ions 184 at opening 164 continuously rises, forming an electrochemical gradient having affinity for tissue 188, in a direction 123.

The constant movement of electrolytic products 144 and accompanying substances into tissue 188 continually depletes the supply of ions 184 at opening 164. However, ions 184 are continually produced by electrolysis of reactant 145 that occurs between (+) 110 and (−) 130 electrodes and the resulting migration of produced ions 184 to opening 164.

The electrochemical gradient, in conjunction with appropriate reactant 145, induces the movement of ions 184 through tissue 188 while accruing electrolytic activity including at least one of the above noted activities of: iontophoresis, electroosmosis, electrolytic desiccation, electokinesis, electro-epilation, and electro-onychomycotomy.

For example, in treating a mycotic nail, reactant 145 would typically consist of a topical anti-mycotic agent, for example miconazole, clotrimazole, econazole, ketoconazole, ciclopirox, naftifine, or terbinafine.

In treating cancer, reactant 145 would consist of at least one anti-cancer agent, for example anti-mitotic agents, photoreactive agents, atomic particle-emitting, antigenically tagged, or genetically altering APIs.

In treating hair 204, for example in hirsute individuals, reactant 145 would include at least one topical epilation agent, for example thioglycolate depilatories of eflornithine. Additionally or alternatively, a Hydroxyl-ion producing reactant 145 would be used to produce (OH−) ions, as described below.

In treating actinic keratosis, reactant 145 would include at least one topical anti pre-cancerous agent, for example Jessner's solution, trichloroacetic acid, bleomycin, hydroxyurea or 5-fluorouracil (5-FU).

Additionally, in treating hyperhydrosis, reactant 145 would optionally include a sweat gland desiccant, for example an aluminum chloride-containing agent.

In an exemplary embodiment, electrolytic reactant 145 comprises an electrolytic therapeutic agent, for example an API that travels through pad 146 and tissue 188 through iontophoretic action, forming product 144 in tissue 188.

In some embodiments, for example in treating full thickness skin ulcerations, therapeutic agent 145 comprises an electrolyte desiccant that forms in tissue 188 and dries tissue 188.

Additionally or alternatively, for example an infected full thickness ulcer, reactant 145 comprises a solution containing a combination of an electrolytic agent and a separate non-charged therapeutic agent.

In some exemplary embodiments, therapeutic agent 145 travels through pad 146 and into tissue 188 through an electro-osmotic gradient induced by the electrolytic ions 184.

In some treatment embodiments, reactant 145 forms product 144, for example having substantially the same chemical formula and/or composition as reactant 145. In other embodiments, product 144 has a different formula and/or composition from reactant 145; the difference being induced, for example, through interaction with tissue 188.

Using certain agents, product 144 accumulates in the interstitial of tissue 188; herein an interstitial product 144. In other embodiments, product 144 accumulates within the cells of tissue 188; herein an intracellular product 144.

Figure 9:
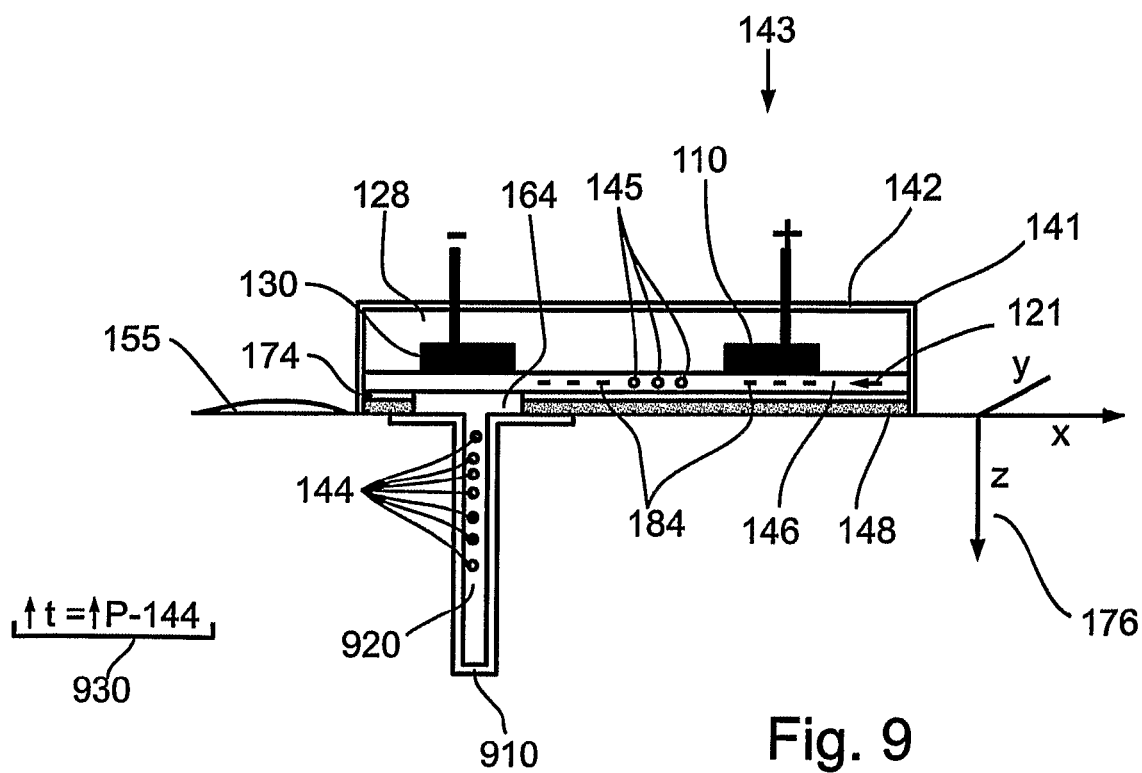
FIG. 9 is a schematic representation of a testing setup, in conjunction with the ECD of FIG. 1, in accordance with an embodiment of the present invention.

As seen in FIG. 9, a testing apparatus, built by the inventor, includes a polyester film 910 that substantially blocks a large portion of window 164 while allowing migration of electrolyte product 144 into a strip of paper 920.

Formula 930 summarizes typical results that accrued: with greater time (t) there was greater penetration (p) of products 144 into paper 920. It is hypothesized that paper 920 roughly corresponds to tissue 188 (FIG. 1). Using such an assumption, the application time of ECD-2 143 will similarly cause greater penetration of product 144 into tissue 188.

While the basis for the relationship between depth and time is not known, it is postulated that electrolytic products 144 initially are deposited in superficial areas of paper 920, corresponding to tissue 188. As electrolytic products 144 concentrate in the superficial level, the superficial level becomes substantially electrically buffered, and products 144 find a path of great electrochemical conductivity at a second, deep level. In this manner, the depth of reactant 144 is postulated to continually increase with time.

As relatively small opening 164 in cross sectional area, herein relatively small opening 164, appears to increase the speed of infusion into tissue 188. Additionally, a relatively small opening 164 appears to focus the deposition of products 144.

For example, when opening 164 is relatively small, reactants 144 form a relatively narrow column extending into tissue 188. The relationship between the size of opening 164, focus of products, and speed of deposition, allows a variety of ECD-2 143 units to be designed, each for a specific application.

For example, in hyperhydrosis treatments, described below, an enlarged opening 164 is beneficial in rapidly treating large areas of over-perspiration; and in onychomycotic treatment, described below, a specially shaped opening 164 is beneficial in focusing product 144 to the long, narrow matrix when the infection source is located within the proximal nail fold.

In some embodiments, additional housing 141, for example comprising a metal, serves to increase to strength and/or further electrically isolate 2-ECD 143, for example allowing submersion in tissue, for example in electro-epilation and deep tumor treatment.

Embeddable ECD

Figure 8:
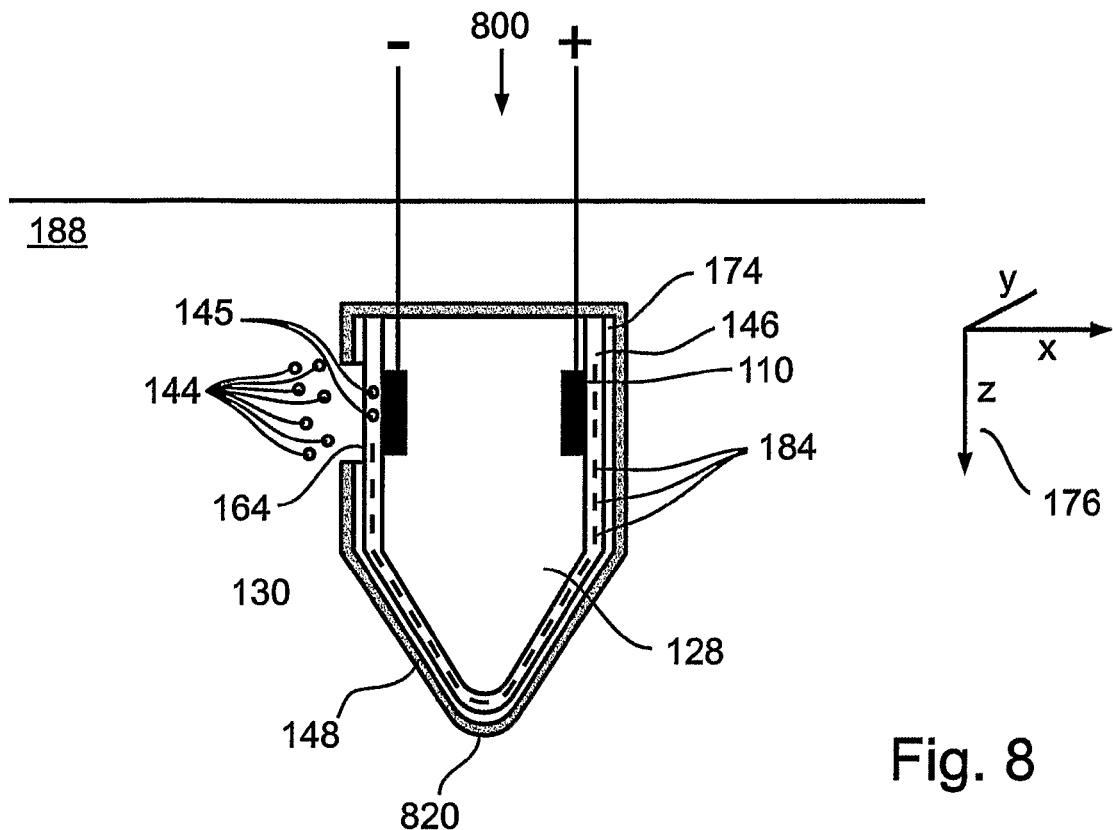
FIG. 8 is a schematic representation of an implantable ECD, in accordance with an embodiment of the present invention.

In an exemplary embodiment, as seen in FIG. 8, 2-ECD 800 includes a single, contiguous base layer 148, that allows embedding within tissue 188. Optionally, ECD-2 800 includes a tapered, or needle-like nose 820 that facilitates penetration, piercing through, and/or placement within tissue 188.

To place 2-ECD 800 in vivo, for example in internal organs such as the liver, a laparoscope is typically used along with minimal incisions; the combination of 2-ECD 800 and a laparoscope yielding fast treatment, healing and minimal post-operative scarring.

In an exemplary embodiment reactant 144 used in treating liver cancer comprises antigenically tagged anti-cancer agents. 2-ECD 800 renders tagged product 145 highly effective by causing significant and rapid concentration in the tumor tissue rather than spreading throughout tissue 188; reducing side effects resulting from less focused and/or systemic dissemination of anti-cancer APIs.

Alternatively, 2-ECD 800 can be implanted in soft tissue, bone, cartilage and fluid areas (e.g., the bladder). Optionally, at least a portion of second base layer 148 comprises aluminum, stainless steel, noble metal, or plastic.

In some embodiments, particularly those used in long-term implantation where 2-ECD 800 integrity is important; base layer 148, insulation layer 174, pad 146, and upper insulation layer 128 are of a planar laminate. Optionally, the laminated construct is substantially flexible.

Flexibility of 2-ECD 800 can be important in implantation in joints, for example the knee, when performing electrolytic treatments of cartilage ions. Due to the motion of the knee, 2-ECD 800 requires flexibility to prevent damage to a joint surface. Flexibility is also required for applications to tissue 188 having boney prominences, for example over the knee joint.

System 200

Figure 2:
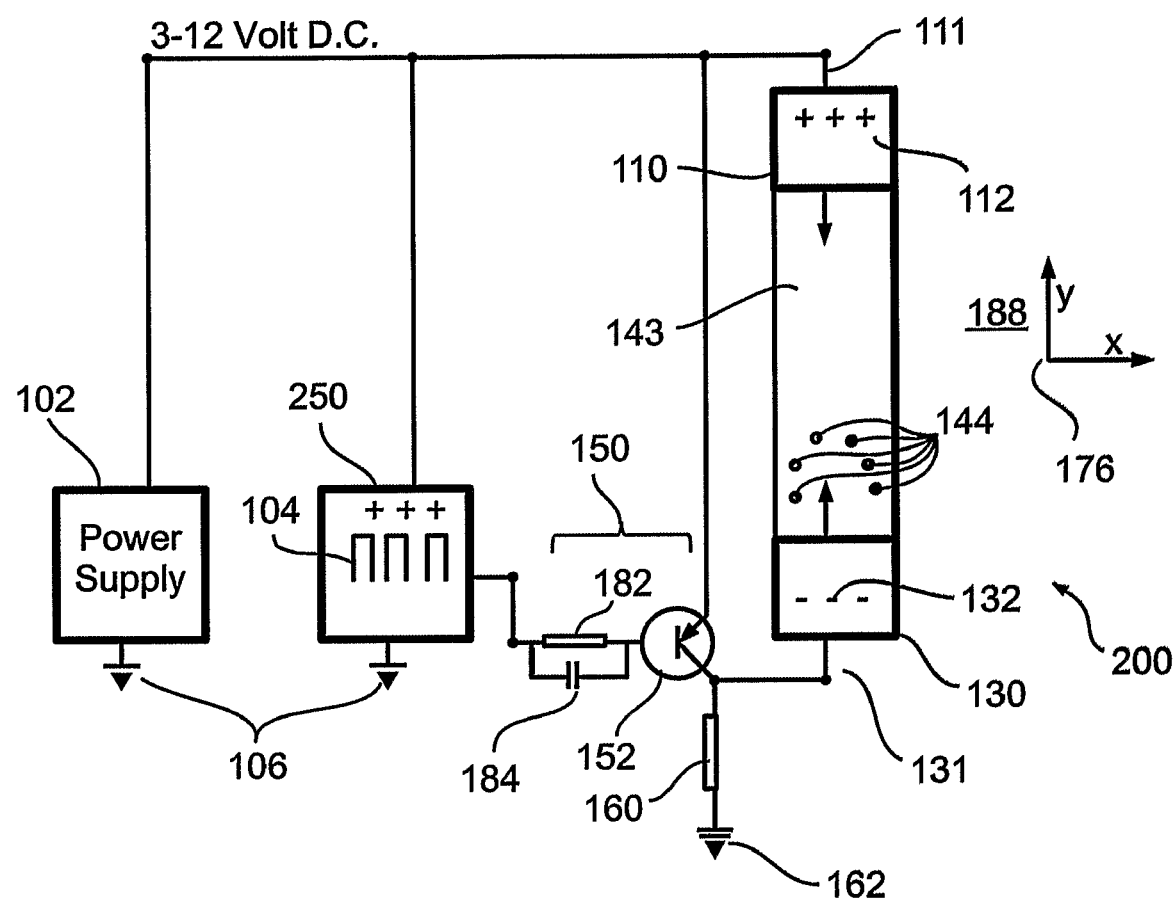
FIG. 2 is a schematic representation of an electrolytic circuit in conjunction with the ECD of FIG. 1, in accordance with an embodiment of the present invention.

As noted, in addition to continuous DC, 2-ECD 143 is capable of receiving pulsed DC as in System 200, shown in FIG. 2. In exemplary embodiments, system 200 includes a power supply 102, having a ground 106.

Power supply 102 comprises an AC to DC converter that provides at least about 1 volt; at least about 2 volts; at least about 4 volts; or at least about 6 volts. Alternatively, power supply 102 provides no more than about 40 volts; no more than about 60 volts; no more than about 80 volts; or no more than about 100 volts. Alternatively, power supply 102 comprises one or more DC batteries.

Oscillator 250 receives power from power supply 102 and, in turn, delivers an electric signal 104 comprising monopolar (+) pulses to a signal amplifier 150.

Pulsed current has, for example, a pulse width of at least about 0.1 second; at least about 0.01 second; at least about $1 \times 10^{-5}$ seconds; or at least about $3 \times 10^{-9}$ seconds.

Alternatively, pulsed current has, for example, a pulse width of no more than about 0.1 seconds; no more than about 0.01 second; no more than about $1 \times 10^{-5}$ seconds; or no more than about $3 \times 10^{-9}$ seconds.

After receiving pulsed current from oscillator 250, signal amplifier 150 amplifies current to at least about 0.1 mA, at least about 2 mA, at least about 3 mA, or at least about 4 mA.

Alternatively, signal amplifier 150, for example, amplifies current to no more than about 100 mA, no more than about 250 mA, no more than about 500 mA, or no more than about 1000 mA.

Signal amplifier 150 typically comprises: resistor 182, capacitor 184, and transistor 152; transistor 152 being connected to a resistor 160 having a ground 162.

Electrodes 110 and 130 typically are connected to terminals 111 and 131 respectively, thereby receiving current from power supply 102. Electrodes 110 and 130 typically dispense a relatively high monopolar pulsed electric current, fluctuating between 0 volts and plus (+) 3 volts. Optionally, power supply 102 fluctuates from at least about 1 volt; at least about 2 volts; at least about 4 volts; at least about 6 volts; or at least about 40 volts. Additionally, power supply 102 optionally fluctuates up to no more than about 40 volts; no more than about 60 volts; no more than about 80 volts; or no more than about 100 volts.

Variations in voltage are typically influenced by the potential ionic properties of reactant 145 (FIG. 1); the desired depth of penetration; and/or the type of tissue 188 being treated (FIG. 1).

In an exemplary embodiment, oscillator 250 is adapted to produce a pulse width comprising $1 \times 10^{-2}$ seconds to $1 \times 10^{-5}$ seconds and/or $1 \times 10^{-5}$ seconds to $3 \times 10^{-9}$ seconds.

In some embodiments, oscillator 250 forms monopolar pulses at a frequency range of between 100 kHz and 300 MHz, a range that:

a) does not stimulate nerves and muscles even at relatively high voltage; and b) facilitates significant deposition of electrolytic products 144 preferably without causing pain or tissue damage.

Additionally, the current frequency produced by oscillator 250 is optionally altered to favor concentration of products 144 at specific depths and/or structures within tissue 188.

In an exemplary embodiment, a frequency of 10 MHz is used for superficial structure treatment, for example hyperhydrosis and hair removal; 1 MHz is used for intermediate depth treatments, for example actinic keratosis; and 300 kHz is used for deep structures, for example inflammatory bursae; the latter treatment being of a depth that often involves convection flow, due to heat production.

Signal Generation

Figure 3:
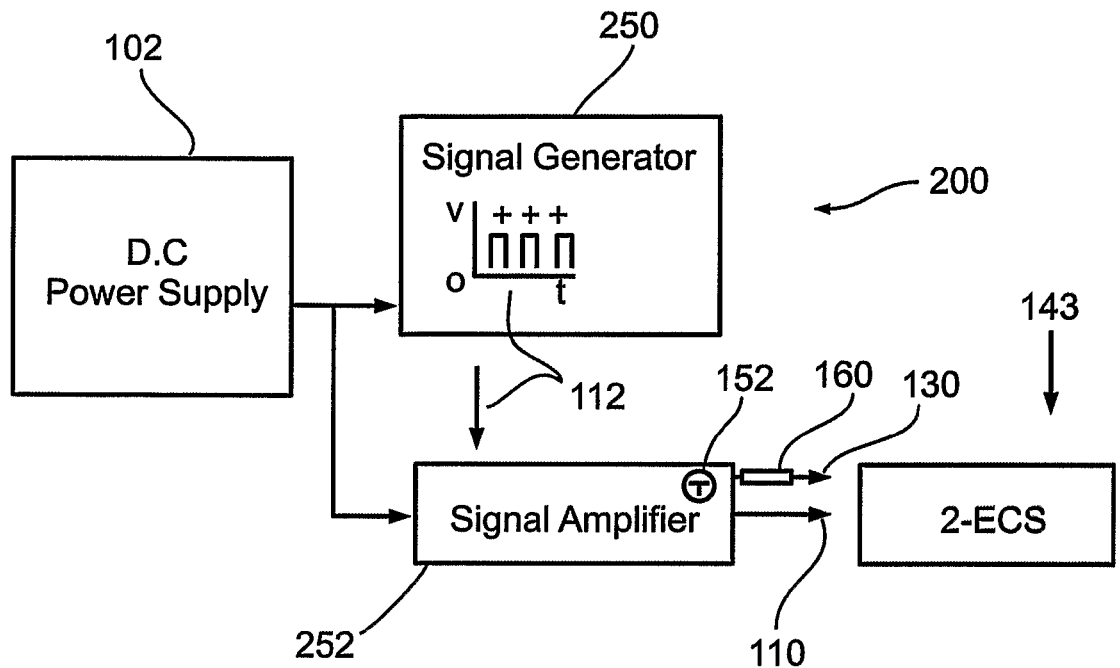
FIG. 3 is a block diagram of the circuit and Device of FIG. 2, in accordance with an embodiment of the present invention.

FIG. 3 shows a schematic diagram of System 100 in which power supply 102, comprising an AC/DC converter, supplies DC between 0 and 12 volts to signal generator 250. Signal generator 250 produces a high frequency monopolar electric signal that fluctuates between 0 and (+) 3-12 volts. The voltage is amplified at signal amplifier 252 to increase amperage to 50-300 mA and delivered to electrodes 110 and 130.

Three Electrode Devices

Figure 4:
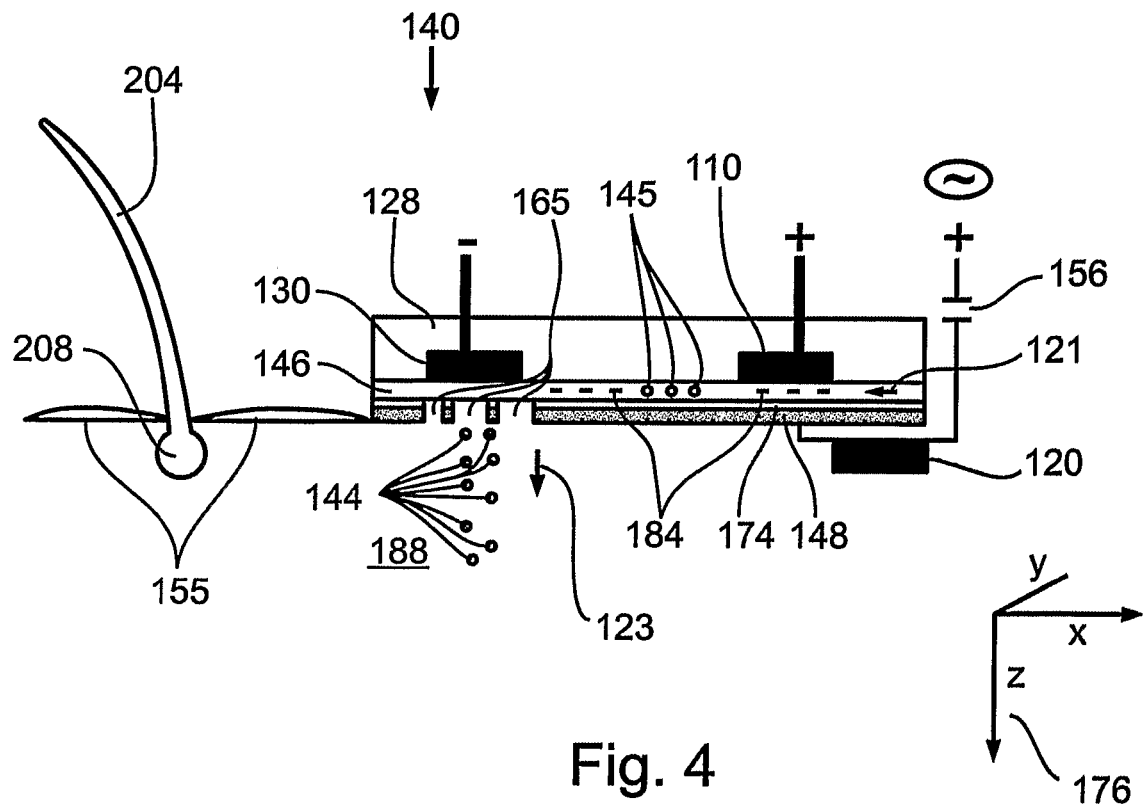
FIG. 4 is a schematic representation of an ECD having three electrodes, in accordance with an embodiment of the present invention.

Referring to FIG. 4, 3-ECD 140 includes all components of 2-ECD 143 with the addition of a side electrode 120 that is connected to a plus DC via a capacitor 156, thereby fostering the production of superficial AC Side electrode 120 producing AC appears to increase kinetic movement of product 144, thereby aiding in deposition of product 144.

In an exemplary embodiment, AC from side electrode 120 appears to enhance deposition of product 144 while remaining primarily on the surface of tissue 188. It is postulated that for this reason AC from side electrode 120 appears to function without negatively impacting the chemo-electric gradient in tissue 188 or the deposition of electrolytic product 144.

System 300

Figures 5, 6:
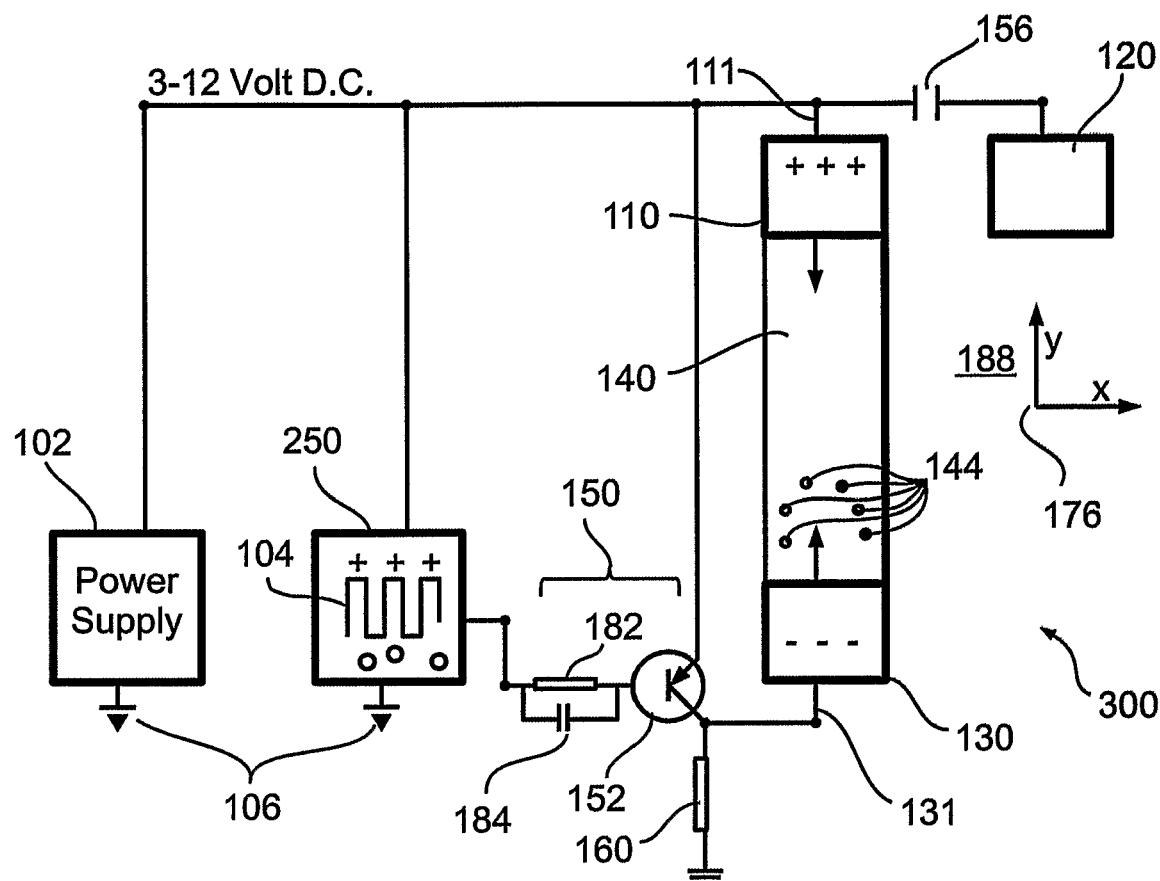
FIG. 5 is a schematic representation of an electrolytic circuit in conjunction with the ECD of FIG. 4, in accordance with an embodiment of the present invention.
FIG. 6 is a schematic representation of an ECD having four electrodes, in accordance with an embodiment of the present invention.

Referring to FIG. 5, system 300 uses substantially the same circuitry as that of 2-ECD 143 (FIG. 2), with the addition of side electrode 120 connected to (+) current through a capacitor 156.

The net effect of current flow to side electrode 120 appears to produce a mild superficial AC that enhances tissue absorption. System 300 appears to have promise in transdermal API delivery, providing increased API penetration and treatment speed.

Four Electrode Device

Referring to FIG. 6, 4-ECD 195, includes two sets of (+) and (−) electrodes:

First (+) 130 and second (−) 110 electrodes in a first set; and

Third (+) 120 and fourth (−) 190 electrodes in a second set.

In some exemplary embodiments:

(+) electrode 130 is positioned over an opening 165, forming (+) ions 185 and electrolytic products 147 from a reactant 149; and third (+) electrode 120 is positioned over opening 164, forming (−) ions 184 and electrolytic products 145 from reactant 145.

The above-noted arrangement is useful, for example, when two products 144 and 147 having opposite polarity are used in the same treatment.

Alternatively, when treatment requires two products 144 and 147 having, for example, the same polarity, but that need to combine in tissue 188, (−) electrodes 110 and 190 are positioned over openings 165 and 164 respectively.

In still another embodiment, pads 170 and 180 (FIG. 7) have the same polarity, but the electrical potential of pad 170 is different from the electrical potential of pad 180. In an exemplary embodiment, a third reactant 175 is used in this latter embodiment in which reactant 175 comprises a catalyst that serves to activate products 144 and 147.

Optionally, catalyst 175 additionally has electrokinetic properties and is introduced onto tissue 188, for example by injection. As defined above, an electrokinetic substance responds to differences in electrical potential.

In an exemplary embodiment, products 144 and 147 are deposited in two separate areas and, for example, diffuse toward one another. At the same time, an electrokinetic catalyst product 179 is deposited in a third area, for example between products 144 and 147 so that as all three products 175, 144 and 147 combine, catalyst cause products 144 and 147 to catalyze into product 179.

Implementation of the three-product migration scenario noted above is useful, for example, in treating brain lesions in which catalyzed products will not pass through the blood brain barrier (BBB). By introducing precursor reactants that pass through the BBB, and applying 2-ECD 400, to a topically accessible area of the brain, for example the brain stem, reaction takes place within brain tissue and supplies necessary reactant 145 including the necessary therapeutic entities.

System 400

Referring to FIG. 7, system 400 is a schematic depiction of circuitry that includes 4-ECD 195. Similar to prior systems, gateway 150 distributes DC pulses to electrodes 110 and 130 on a Device portion 180. A second gateway 151 distributes. DC pulses to electrodes 120 and 190 on a second Device portion 170.

Additionally, a third gateway 153 is positioned between portions 180 and 170 to ensure separation of the currents, pulse width and voltage so that each of portions 180 and 170 function independently. Alternatively, gateway 153 causes a shift of in pulse so that when current pulse is present at 180, at 170 the pulse is absent, and vice versa.

Biological Applications

Before explaining additional biological applications of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

This invention has multiple biological applications well beyond those presented, the many additional applications and/or modifications to the invention for each application being known to those familiar with the art.

Electro-Epilation

Referring to FIG. 1, as noted above, hair 204 grows from a follicle 208, which is not fully keratinized and therefore rapidly absorbs electrolytic products.

Reactant 184 comprises, for example, a salt of NaCl or KCl. (OH−) ions from reactant 144 form at electrode (−) 130, while (H+) acid forms at electrodes (+) 110. In an exemplary embodiment, follicle 208 absorbs (OH⁻) ions from reactant 144 that are in liquid form, thereby causing poisoning of follicle 208.

Only a small amount of (OH⁻) ions from reactant 144 is needed, due to the small size of follicle 208. The high pH gradient is maintained as long as the electrochemical reaction takes place. The speed of reaction, for example, can be reduced by adding a buffer to reactant 184.

In an alternative embodiment, a needle extending from electrode (−) 130 having a similar structure to the 2-ECD 800, FIG. 8, is placed relatively close to follicle 208 to cause ionic changes within follicle 208 without the intermediary of reactant 184.

In an exemplary electrolysis embodiment, nose 820 is sharp to facilitate entry into tissue and opening 164 is positioned near or within pointed nose 820. Optionally, pad 146 contains reactants 145 that produce OH⁻ and $H_2$.

Poisoning of follicle 208 with OH⁻ appears to occur in the anagen and telogen phases, but not in catagen phase. However, it is likely that a catagen phase follicle 208 is likely to be poisoned by delivering an appropriate electrolytic product 144 other than OH⁻; with dual products 144 being readily delivered by a 2-ECD 800 as described above. Thus, using 2-ECD 800 or other embodiments, treatment of all three phases of follicular 208 growth could arrested in a single treatment.

Onychomycosis

Using System 200 (FIG. 1), treatment of onychomycosis following nail avulsion would use an appropriate topical reactant comprising a standard topical anti-mycotic agent, for example: amorolfine, ciclopirox olamine, sodium pyrithione, bifonazole/urea, propylene glycol-urea-lactic acid, imidazoles, or allylamines. To facilitate a well-focused and deep deposition that is appropriate for the nail fold, base 148 and insulating layer 174, in addition to the shaped opening 164 noted above, comprise a curvature and/or a flexible material to ensure conformation to the nail layer curvature.

While the above-noted treatment has not been performed, it is postulated that 2-ECD 143 will facilitate efficient intracellular deposition of product 145 so that treatments can be limited to once a week until the nail appears clear of infection.

Hyperhydrosis

System 400 (FIG. 7) is optionally used in treating multiple tissue types for the purpose of treating primary hyperhydrosis.

While at the present time, the most efficacious combination of current, voltage and/or pulse width is unknown, system 400 provides the option of providing two different electrical currents and/or electrolytic reactants 145, a first tailored to affect eccrine glands and a second tailored to affect apocrine glands; thereby greatly increasing effectiveness in addition to the exceptional speed of 4-ECD 195.

Additionally, it is postulated that 3-ECD 140, with AC side electrode 120, has the potential to also affect multiple types of tissue 188.

Surface Tumor Treatment

Using 3-ECD 140, a surface tumor, for example squamous cell carcinoma in situ, would likely respond to electrolytic desiccation treatments using similar techniques as those previously described for single electrode pair used in hyperhydrosis treatments.

It is expected that during the life of this patent many relevant delivery systems will be developed and the scope of the term AC Tissue Treatment is intended to include all such new technologies a priori.

As used herein the term "about" refers to ±10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

What is claimed is:

1. An apparatus for providing electrolytic tissue treatment, comprising:
    a) a reactant, at least a portion of said reactant being electrolysable;
    b) a pad including said reactant, said pad having a lower pad surface;
    c) a first electrically insulating layer having an upper insulation surface substantially in contact with said lower pad surface and a first opening passing through said first electrically insulating layer;
    d) a first terminal and a second terminal, configured for connecting to a direct current power source;
    e) at least two electrodes substantially contacting said pad and spaced a distance from each other, such that a first electrode connected to said first terminal contacts said pad substantially proximate to said first opening and a second electrode connected to said second terminal contacts said pad substantially distant from said first opening;
    said first insulating layer includes a lower surface substantially in contact with a first base layer, said first base layer having a first opening substantially aligned with said insulation layer first opening;
    wherein said apparatus further comprising:
    a second electrically insulating layer, where said at least two electrodes and said pad are contained between said first electrically insulating layer and said second electrically insulating layer; and
    a second base layer substantially covering said second insulating layer.

2. The apparatus of claim 1, wherein said pad is substantially soaked with said reactant.

3. The apparatus according to claim 1, wherein said reactant includes at least one of i) an active pharmaceutical ingredient and ii) a salt.

4. The apparatus according to claim 1, wherein said second electrically insulating layer is substantially contiguous with said first electrically insulating layer, thereby together substantially containing said pad and said at least two electrodes, and said second base layer is substantially contiguous with said first base layer, thereby substantially electrically sealing at least a portion of said first and second insulating layers.

5. The apparatus according to claim 4, wherein said upper insulation layer, said pad, and said lower insulation layer constitute a laminated construct.

6. The apparatus according to claim 5, wherein said laminated construct is substantially flexible.

7. The apparatus according to claim 6, wherein said first insulating layer comprises at least two angulated walls defining an internal volume therebetween, wherein said first electrode, said second electrode and said pad are contained within said volume.

8. The apparatus according to claim 7, wherein said at least two angulated walls substantially form a needle-like configuration.

9. The apparatus according to claim 8, wherein said needle-like configuration is configured to pierce tissue.

10. The apparatus according to claim 1, wherein said apparatus is substantially implantable in vivo.

11. An apparatus for providing electrolytic tissue treatment, comprising:
   a) a reactant, at least a portion of said reactant being electrolysable;
   b) a pad including said reactant, said pad having a lower pad surface;
   c) a first electrically insulating layer having an upper insulation surface substantially in contact with said lower pad surface and a first opening passing through said first electrically insulating layer;
   d) a first terminal and a second terminal, configured for connecting to a direct current power source;
   e) at least two electrodes substantially contacting said pad and spaced a distance from each other, such that a first electrode connected to said first terminal contacts said pad substantially proximate to said first opening and a second electrode connected to said second terminal contacts said pad substantially distant from said first opening;
   said first insulating layer includes a lower surface substantially in contact with a first base layer, said first base layer having a first opening substantially aligned with said insulation layer first opening;
   wherein at least a portion of said first base layer is electrically conductive.

12. The apparatus according to claim 3, further comprising a side electrode in electrical contact with said electrically conductive portion of said first base layer.

13. The apparatus according to claim 12, including an alternating current power supply connected to said side electrode, said side electrode thereby producing an alternating electrical field.

14. A method for treating an in vivo portion of tissue, the method comprising:
   i) positioning a pad proximate to an in vivo portion of tissue;
   ii) adding a reactant to said pad;
   iii) contacting said pad with a first electrode so that said first electrode is proximate to said portion of said pad proximate to said in vivo portion of tissue;
   iv) contacting said pad with a second electrode so as to provide an electrical path between said first electrode and said second electrode through said reactant;
   v) passing a direct current through a circuit including said first electrode, said reactant and said second electrode, thereby forming, proximate to said first electrode, at least one of an electrolytic effect and an electrolytic product of said reactant
   wherein said method further including:
   i) providing a side electrode in contact with said in vivo tissue portion;
   ii) applying an alternating current to said side electrode thereby enhancing said electrolytic effect.

15. The method according to claim 14, wherein said second electrode is electrically distanced from said portion of in vivo tissue so as to substantially prevent passage of current through said portion of in vivo tissue.

16. The method according to claim 14, wherein during said passing of said direct current, said electrolytic product:
   migrates to form a chemoelectric gradient proximate to said first electrode along a surface of said portion of in vivo tissue; and
   penetrates a first distance below the surface of said portion of in vivo tissue.

17. The method of claim 14 comprising: substantially implanting said pad or both said pad and said electrodes in a subject.

18. A method for cosmetically improving an area of unaesthetic skin using an electrolytic treatment, comprising:
   i) positioning a pad proximate to an area of unaesthetic skin;
   ii) contacting the pad with a first electrode and a second electrode;
   iii) interposing an insulating layer between said skin and said second electrode; and
   iv) passing a direct current of at least about 1 mA between said first and second electrodes, thereby cosmetically improving the area.

19. The method of claim 18 wherein the method comprises epilation, and the methods further comprising:
   substantially saturating said pad with at least one reactant, wherein said at least one reactant comprises an epilation active pharmaceutical ingredient.

20. A method for epilation comprising:
   i) positioning a pad proximate to an area of skin, wherein said pad includes at least one reactant;
   ii) contacting said pad with a first electrode and a second electrode;
   iii) interposing an electrically insulating layer between said skin and said second electrode; and
   iv) passing a direct current of at least about 1 mA between said first and second electrodes thereby epilating the area of skin proximate to said pad.

21. The method of claim 20, wherein said at least one reactant comprises an epilation active pharmaceutical ingredient.

22. The method of claim 20, wherein said pad proximate to said skin is flexible.

* * * * *